(12) United States Patent
Smith et al.

(10) Patent No.: US 10,221,188 B2
(45) Date of Patent: Mar. 5, 2019

(54) ISOIDIDE MANUFACTURE AND PURIFICATION

(71) Applicant: Archer Daniels Midland Company, Decatur, IL (US)

(72) Inventors: Brennan Smith, Decatur, IL (US); Josh Terrian, Lovington, IL (US)

(73) Assignee: Archer Daniels Midland Company, Decatur, IL (US)

( * ) Notice: Subject to any disclaimer, the term of this patent is extended or adjusted under 35 U.S.C. 154(b) by 81 days.

(21) Appl. No.: 15/552,655

(22) PCT Filed: Feb. 19, 2016

(86) PCT No.: PCT/US2016/018627
§ 371 (c)(1),
(2) Date: Aug. 22, 2017

(87) PCT Pub. No.: WO2016/137833
PCT Pub. Date: Sep. 1, 2016

(65) Prior Publication Data
US 2018/0044349 A1 Feb. 15, 2018

Related U.S. Application Data

(60) Provisional application No. 62/119,936, filed on Feb. 24, 2015.

(51) Int. Cl.
*C07D 493/04* (2006.01)
*B01J 25/02* (2006.01)
*B01D 15/18* (2006.01)
*B01D 15/36* (2006.01)
*C13K 13/00* (2006.01)

(52) U.S. Cl.
CPC ......... *C07D 493/04* (2013.01); *B01D 15/185* (2013.01); *B01D 15/362* (2013.01); *B01J 25/02* (2013.01); *C13K 13/00* (2013.01); *C13K 13/007* (2013.01)

(58) Field of Classification Search
None
See application file for complete search history.

(56) References Cited

PUBLICATIONS

LeNotre et al ChemSusChem 2013, vol. 6, pp. 693-700.*

* cited by examiner

*Primary Examiner* — Heidi Reese
(74) *Attorney, Agent, or Firm* — William B. Miller

(57) ABSTRACT

Methods are provided for the conversion of isosorbide to isoidide, wherein the isosorbide contains sorbitan impurities. The impurities in the isosorbide subjected to epimerization are converted to hydrodeoxygenation products. A method for synthesizing isoidide, comprising, providing an isosorbide containing one or more sorbitans; and, epimerizing the isosorbide to form an epimerization product comprising isoidide and hydrodeoxygenation products.

11 Claims, 2 Drawing Sheets

ISOIDIDE MANUFACTURE AND PURIFICATION

PRIORITY CLAIM

The present application is a 371 National Phase Entry of International Patent Application PCT/US2016/018627 filed Feb. 19, 2016, which claims benefit of priority of U.S. Provisional Application No. 62/119,936, filed on Feb. 24, 2015, the contents of which are incorporated herein.

FIELD OF INVENTION

The present invention relates to synthesis and purification of isohexides. In particular, the present invention is concerned with synthesis and purification of isoidide.

BACKGROUND

There are fundamentally three isohexides: isomannide, isoidide, and isosorbide. Isosorbide is a commercially-produced, bicyclic diol that is easily available from biological feedstock. Glucose can be hydrogenated to sorbitol. The latter, in turn, can be subjected to double dehydration so as to yield isosorbide. Its double hydroxyl function would make isosorbide of interest as a building block for polymerization. However, the making of polymers of suitable properties from isosorbide is hampered by the molecule's stereochemistry, since the two hydroxyl groups are directed to different sides of the molecule's plane. i.e., the up to now more easily obtainable isosorbide is unsymmetrical with one endohydroxyl group and one exo-hydroxyl group, resulting in asymmetrical reactivity and amorphous polymers (due to the lack of symmetry). Its epimer isomannide, which has two endo-hydroxyl groups, has proven to be unfavorable for polymerization due to low reactivity and low linearity. On the other hand, the epimer isoidide has two exo-hydroxyl groups, and has been viewed as far better suited for use as a building block for polymerization than either isosorbide or isomannide. The symmetrical structure of isoidide eliminates the regiochemical reactivity difference between the two hydroxyl functionalities.

Examples of polymers wherein isoidide would be suitably used as a building block include polyesters made by polycondensation of isoidide and a dicarboxylic acid or anhydride, and polycarbonates made by reaction with a bifunctional carboxyl compound such as phosgene. Isoidide would also be suitably used in other polymerizations wherein conventionally other diols are used. E.g., bisglycidyl ethers of isoidide can be used as a substitute for bisphenol-A in epoxy resins. Isoidide has also been used or proposed for use in place of petroleum-based monomers such as terephthalic acid, for instance. Exemplary processes for isoidide polymerization, particularly, semi-crystalline isoidide furanoate homopolyesters, are set forth in co-pending PCT Patent Application Publication No. WO2015166070 A1, published Nov. 5, 2015, "Polyisoidide Furanoate Thermoplastic Polyesters and Copolyesters."

Isoidide, however, is not currently manufactured on a commercial scale, in part (but not exclusively) because of the high cost of the synthetic precursor iditol from which isoidide might be made by an analogous double dehydration pathway as employed for making isosorbide. Sorbitan isomers include 1,4-sorbitan monoanhydrohexitol (1,4-anhydrosorbitol), 3,6-anhydrosorbitol, 2,5-anhydrosorbitol, 1,5-anhydrosorbitol and 1,4,3,6-dianhydrosorbitol.

An alternative pathway to isoidide through the epimerization of isosorbide has been investigated as a way of getting around this difficulty, though the literature related to this alternative pathway is quite limited. In one recent publication, LeNotre et al. reported a highly efficient method for obtaining highly pure, resin-grade isoidide through catalytic epimerization of isosorbide using a ruthenium-on-carbon catalyst (LeNotre et al. "Synthesis of Isoidide through Epimerization of Isosorbide using Ruthenium on Carbon" ChemSusChem 6, 693-700, 2013). This reference shows the synthesis of isoidide from highly purified (>99.5% pure) isosorbide (Polysorb, Roquette, Lestrem, France).

Co-pending and commonly-assigned International Patent Application No. WO2013125950A1, filed Feb. 20, 2012 for "Method of making isoidide" (the "WO'950 application" or "WO'950"), such application being incorporated herein by reference in its entirety, is related and describes a process for the preparation of isoidide from isosorbide, wherein an aqueous solution of isosorbide is subjected to epimerization in the presence of hydrogen under the influence of a catalyst comprising ruthenium on a support, at a starting pH of above 7. WO'950 further provides a process for the preparation of isoidide from glucose by hydrogenating glucose to form sorbitol, dehydrating the resulting sorbitol to form isosorbide, then epimerizing the isosorbide into isoidide using a catalyst comprising carbon-supported ruthenium.

One challenge that this alternative pathway encounters is that the epimerization product exists as a mixture of three isohexides: isosorbide, isoidide and isomannide. The separation of these isomers has generally been by fractional distillation. While distillation is effective to a certain extent, the isohexides have relatively close boiling points at elevated temperatures and reduced pressures. This results in added cost and complexity. A related further challenge to the practical commercial fulfillment of this alternative pathway has been the difficulty, in light of the very high purities demanded by polymer manufacturers for monomer feedstocks, of producing a highly pure isosorbide feed to the epimerization process in the first place. The conversion of sorbitol to isosorbide by an acid-catalyzed double dehydration has been hampered by vexing side reactions in which unwanted by-products are formed; consequently, vigorous effort has been exerted (albeit largely for the purpose of producing and selling a monomer grade isosorbide rather than a monomer grade isoidide product) to develop methods whereby the side reactions are diminished. As taught by PCT Patent Application Publication WO0239957, published Sep. 6, 2002, a number of byproducts are formed during the production of isosorbide from sorbitol; conventional wisdom heretofore held that isosorbide must be separated from these before conversion to isoidide. These unwanted byproducts include, but are not limited to, monoanhydrides (notably 2,5-anhydro-D-mannitol; 2,5-anhydro-L-iditol; sorbitan (1,4-anhydro-D-glucitol); and 3,6-anhydro-D-glucitol), dimers of the monoanhydrides, and oligomeric compounds.

For example, in co-pending and commonly-assigned International Patent Application No. WO 2013138153, published Sep. 19, 2013 for "Process for making sugar and/or sugar alcohol dehydration products," a process is disclosed for making one or more sugar dehydration products from an aqueous sugars solution including one or more of pentoses and hexoses. The aqueous sugars solution is subjected to an acid-catalyzed dehydration at an elevated temperature using a substituted sulfonic acid catalyst with low water solubility but which is solubilized in the aqueous sugars solution at the elevated temperature. Additionally, one or more dehydration products are made from an aqueous sugar alcohols solution including one or more of the alcohols from pentoses and hexoses, by subjecting the aqueous sugar alcohols solution to an acid-catalyzed dehydration at an elevated temperature using a substituted sulfonic acid catalyst with low water solubility but which is solubilized in the aqueous sugar alcohols solution at the elevated temperature.

In another background reference, co-pending and commonly-assigned International Patent Application No. WO 2014070371 A1, published May 8, 2014 for "Improved method of making internal dehydration products of sugar alcohols," compositions having reduced color and/or color stable on storage under generally prevailing storage conditions, including isosorbide, are disclosed.

Another approach for managing color problems in isosorbide synthesis is disclosed in copending and commonly-assigned International Patent Application No. WO 2014070369 A1, published May 8, 2014 for "Hydrogenation of isohexide products for improved color." This disclosure elucidates a process for making one or more isohexides, comprising dehydrating one or more hexitols in the presence of an acid catalyst to form a crude dehydration product mixture including one or more isohexides; further processing the crude dehydration product mixture to separate out one or more fractions of a greater purity or higher concentration of at least one of the isohexides in the crude dehydration product mixture and one or more fractions of a lesser purity or concentration; and hydrogenating at least one of: a) the crude dehydration product mixture; b) a neutralized crude dehydration product mixture, following a neutralization step performed on the crude dehydration product mixture; c) the product mixture following a neutralization step performed on the crude dehydration product mixture and further following a step conducted on the neutralized crude dehydration product mixture to remove ionic species therefrom; d) a greater purity or higher concentration fraction; and e) a lesser purity or concentration fraction, by reaction with a hydrogen source in the presence of a hydrogenation catalyst, under conditions effective to carry out hydrogenation. In addition, isosorbide is made by dehydrating sorbitol in the presence of an acid catalyst to form a crude isosorbide product mixture, hydrogenating the crude isosorbide product mixture by reaction with hydrogen in the presence of a hydrogenation catalyst, at a hydrogen pressure of at least about 6.9 MPa, and obtaining an isosorbide-enriched product from the hydrogenated crude isosorbide product mixture. Particularly, isosorbide is made by dehydrating sorbitol in the presence of an acid catalyst to form a crude isosorbide product mixture, removing ionic species from the crude isosorbide product mixture by contacting the crude isosorbide product mixture with one or more ion exchange resins, through ion exclusion means or through a combination of ion exchange and ion exclusion means, hydrogenating the crude isosorbide product mixture with ionic species having been removed therefrom, by reaction with hydrogen in the presence of a hydrogenation catalyst; and obtaining an isosorbide-enriched product with improved color from the hydrogenated crude isosorbide product mixture.

Similarly, copending and commonly-assigned International Patent Application Publication No. WO2014070370, published May 8, 2014 for "Additives for improved isohexide products" addresses the well-known color problem of isosorbide by dehydrating one or more hexitols in the presence of an acid catalyst to form a crude dehydration product mixture, adding one or more antioxidants to the crude dehydration product mixture, and further processing the crude dehydration product mixture containing the one or more antioxidants to yield a product enriched in one or more isohexides compared to the crude dehydration product mixture; the initial AHPA color of the isohexide-enriched products being 100 or less.

Enhanced yields of isosorbide and of the 1,4-sorbitan precursor of isosorbide were obtained in the acid-catalyzed dehydration of sugar alcohols in copending and commonly-assigned International Patent Application No. WO2014137619, Published Sep. 12, 2014 for "Process for acid dehydration of sugar alcohols." These were obtained by acid-catalyzed dehydration of a sugar alcohol, comprising contacting the sugar alcohol with a water-tolerant Lewis acid catalyst at a temperature and for a time sufficient to produce water and at least a partially dehydrated sugar alcohol product. Specifically, isosorbide was produced from sorbitol by contacting sorbitol with an effective amount of homogeneous Lewis acid catalyst such as bismuth (III) triflate, gallium (III) triflate, scandium (III) triflate, aluminum triflate, indium (III) triflate, tin (II) triflate and combinations of two or more of these, at a temperature and for a time sufficient to produce a product mixture including isosorbide.

The color problem inherent in isosorbide synthesis has also been addressed in copending and commonly-assigned PCT Patent Application Publication No. WO2015112389A1, published Jul. 30, 2014 for "Process for producing isohexides". Isohexides are continuously dehydrated in the presence of an acid catalyst under vacuum using a thin film evaporator to produce a crude dehydration product mixture including the isohexide dehydration product from the hexitol. Improved carbon accountability in the dehydration of sugar alcohols and carbon accountability levels greater that 75% have been achieved.

Judicious catalyst selection has enabled development of marked improvements in isosorbide yield, product accountability and color body retrenchment in copending and commonly-assigned International Patent Application Publication No. WO/2015/156846, published Oct. 15, 2015, for "Dehydration of a sugar alcohol with mixed combination of acid catalysts."

Semi-crystalline polyesters from isoidide and 2,5-furandicarboxylic acid are disclosed in co-pending International Patent Application No. WO2015166070 A1, published Nov. 5, 2015, "Polyisoidide Furanoate Thermoplastic Polyesters and Copolyesters." Semi-crystalline copolyesters from isoidide and a minor amount of either 1,4-butanediol or 2,3-butanediol with 2,5-furandicarboxylic acid are also taught, together with processes for making high molecular weight materials by melt polymerization providing a semi-crystalline polymer then performing solid state condensation on the semi-crystalline polymer.

However, as already mentioned above, polymer applications typically require pure monomer feedstocks. One skilled in the art considers it axiomatic that the properties of polymers produced from impure monomers are likely to be inadequate. Impurities in monomers can interfere with the process of polymerization. In addition, color precursors formed as by-products of the synthetic reactions can cause development of color problems in polymers made from isoidide.

In fact, sorbitans are the primary by-products in the isosorbide synthesis from sorbitol, causing significant problems with color development and isosorbide degradation over time. Sorbitans are very undesirable in isosorbide due to the detrimental effects their breakdown products exert on isosorbide. Sorbitans decompose readily in cascades of reactions to form a plurality of poorly-characterized product including furans; these further decompose to form compounds which discolor isosorbide and products produced therefrom. Sorbitans in isoidide are undesirable in most cases; the presence of sorbitan causes yellowing of crystalline isosorbide. Another known set of compounds formed in sorbitan decomposition cascades is organic acids. Organic acids react with isosorbide to break it down into other unwanted impurities, lowering isosorbide content as well. Previously mentioned International Patent Application No. WO 2014070371 A1 achieves the removal of sorbitans from sorbitol by distillation. Further, previously mentioned International Patent Application No. WO 2014070369 A1 cited Japanese patent application as teaching problems associated with the instability of sorbitans in isosorbide: "JP 2006/316025 for its part earlier indicated that the formation of degradation/decomposition products in aged samples of isosorbide was related to auto oxidation of the 1,4-sorbitan monoanhydrohexitol side product and to unspecified "side reactions" involving a solvent (such as water and organic solvents such as xylene and toluene) from the dehydration of sorbitol to make isosorbide. The JP'025 reference prescribes multiple distillations of the crude isosorbide in the absence of a solvent at gradually increasing temperatures and/or at least one such solventless distillation followed by thermal treatment of the isosorbide to reduce the 1,4-sorbitan content of the isosorbide product, with bleaching of the isosorbide product included in each case by treating with ion exchange resins and carbon adsorption."

Perhaps not surprisingly, then, even when highly pure isosorbide is obtained and used in an epimerization process as described by Le Notre et al., a set of by-products are formed that with the isomannide and isosorbide epimers pose still further difficulties for obtaining the ultimately desired monomer grade purity isoidide product. International Patent Application No. WO 2013125950 (the WO'950 application) thus teaches in reference to Le Notre et al.'s proposed process that a method for making isoidide while avoiding side reactions is desirable. They point out that yield-reducing side reactions lead to undesirable mass loss, e.g. as a result of hydrodeoxygenation. The products of these side reactions included non-volatile hydrodeoxygenation (HDO) products. This follows the conventional wisdom that also dictates that side-reactions lead to unwanted by-products, thus reaction catalysts and reaction conditions must be cognizant of, if not focused on, minimizing by-products.

Conventional wisdom inherent in synthetic reactions dictates that side-reactions leading to unwanted by-products should be avoided from a yield-loss perspective. Conventional wisdom would also dictate, as observed previously, that in order to produce high-purity products, high purity starting materials are needed. Fundamental to multi-step reaction procedures is the tenet that the purity of the product of each step is proportional to the purity of the starting material or intermediate reacted in that step. Conventional wisdom also speaks to purification procedures, which should be optimized to give the starting materials and intermediates of high purity.

However, we have now discovered, contrary to these conventional paradigms, that when isoidide is made by epimerization of a starting isosorbide composition in which costly purification steps are skipped so that certain isosorbide reaction by-products have been allowed to remain from an isosorbide containing these certain isosorbide reaction by-products (hereafter, "isosorbide feedstock containing one or more sorbitans")—nevertheless monomer grade-purity isoidide may be made therefrom in unexpectedly good yields.

Independently we have determined that the epimerization of an epimerization reactor feed containing one or more sorbitans, such as an incompletely purified feed mixture, enables certain economies in the downstream separation and purification measures that are needed to produce monomer grade isoidide (where "monomer grade isoidide" is understood herein as an isoidide of at least 99.5 percent purity, while preferably the purity obtained is 99.9 percent or better), in addition to the just-mentioned economies in the upstream generation of an isosorbide feedstock for epimerization.

The great bulk of the literature related to isohexide purification technologies has been developed, again not surprisingly, in the context of the purification of product mixtures from the double dehydration of hexitols. In regard to the production of isosorbide from sorbitol, these product mixtures conventionally all contain isomannide, isosorbide and isoidide, as well as partially dehydrated sorbitans. Nevertheless, the isohexide purification art developed for the purification of hexitol double dehydration product mixtures does represent pertinent art for the task of purifying an epimerization product mixture as produced in an epimerization of isosorbide to provide isoidide.

As summarized in U.S. Pat. Nos. 7,122,661 and 8,008,477, a number of approaches had been suggested previously (that is, previous to these two patents) for obtaining the internal dehydration products (and particularly for obtaining the dianhydrohexitols such as isosorbide especially) in greater purity, for a variety of reasons. Some of these approaches sought improvements in purity through changes to the dehydration process by which the dianhydrohexitols are made, while other approaches involved a form of purification after the dianhydrohexitol compositions are formed.

For example, British Patent No. GB 613,444 describes the production of an isosorbide composition through dehydration carried out in a water/xylene medium, followed by distillation and recrystallization from an alcohol/ether mixture.

International Patent Application No. WO 00/14081 describes distillation and recrystallization from a lower aliphatic alcohol, or distillation alone in the presence of sodium borohydride and in an inert atmosphere.

U.S. Pat. No. 4,408,061 uses gaseous hydrogen halide or liquid hydrogen fluoride dehydration catalysts with carboxylic acid co-catalysts followed by distillation of the crude isosorbide or isomannide compositions thus obtained.

U.S. Pat. No. 7,122,661 for its part describes a process for obtaining isohexide compositions of 99.5% or greater purity and improved storage stability, without necessarily involving a comparatively costly and low yielding post-distillation crystallization step from a solvent medium, through using an ion-exchange step followed by a decolorization treatment step. More particularly, a distilled isohexide composition is described as subjected to treatment with at least one ion-exchange means, which can be a mixed bed of anionic resin(s) and cationic resin(s) or a succession of cationic resin(s) and anionic resin(s), followed by treatment with at least one "decolorizing means". The decolorizing means can be activated charcoal in granular or pulverulent form. In certain embodiments, a second treatment with the decolorizing means is contemplated before the ion-exchange treatment step.

In J. Amer. Chem. Soc. 67 1865 (Oct. 1945), a column of adsorptive clay was proposed for isohexide separation: "A mixture, in disproportionate amounts, of 1,4:3,6-dianhydrosorbitol (isosorbide), 1,4:3,6-dianhydro-D-mannitol (isomannide), and 1,4:3,6-dianhydro-L-iditol (isoidide) was chromatographed to show three zones."

International Patent Application No. WO02/39957 developed a chromatographic approach, operable without heat, for removal of unwanted reaction by-product from isosorbide. To separate isohexides produced by an acid acid-catalyzed hydrolysis of sorbitol (approximate composition by weight of 75% isosorbide) from non-isohexides (10% anhydro by-products (hydrodeoxygenation (HDO) reaction products and 15% dimers/oligomers), they employed acid resins in the protonated (H$^+$) form in simulated moving bed chromatography. However, their acid resins in the protonated form were not able to separate isomers/epimers such as isosorbide from isoidide, as evidenced by the isoidide content in their purified isosorbide, and were certainly not able to obtain a purified isoidide.

Distillation followed by crystallization would likely be the most favored approach, generally speaking, for purifying the isohexide product mixtures from the double dehydration of hexitols. Isoidide purification by crystallization is, however, poorly understood. Early attempts to crystallize a water solution of isoidide by evaporation afforded a syrup from which no crystalline material could be obtained. The completely benzoylated derivative could be fractionally crystallized to give pure isoidide dibenzoylate (Journal of the American Chemical Society (1946), 68, 939-41). Crystallization from solvent of the benzoic acid esters of isoidide was taught in U.S. Pat. No. 3,023,223 (issued Feb. 23, 1962), and benzoyl derivatives and nitrate derivatives were crystallized from solvents in U.S. Pat. No. 4,721,796 (issued Jan. 26, 1988), but isoidide was not crystallized in either patent. Anhydrous sugar alcohol was crystallized from ethanol (Abstracts, Japanese Patents No. JP5492497 and JP5492531, both issued May 14, 2014). An alternative approach is presented in International Patent Application No. WO 01/81785, published Jun. 21, 2012, which teaches the addition of a saccharide distillation aid to a reaction product of mixed anhydrosugar alcohols (isosorbide, isomannide, isoidide) followed by distillation, such as at 220° C. under a vacuum of 3 mm Hg. The saccharide reportedly increases the flow properties of the system; separation of isoidide from isosorbide was not taught. Distillation is also employed in International Patent Application No. WO 14/73843, published May 15, 2014 to obtain "anhydrosugar alcohol (in particular, isosorbide, isomannide, isoidide, and the like) having a purity of 98 percent or higher and containing less than 0.1 percent of sorbitol and a sorbitan isomer, which are impurities, in a high total distillation yield of 94 percent or higher." This is accomplished by "distilling the converted liquid over two or more stages by sequentially using a combination of an external condenser type wiped film evaporator and an internal condenser type short path evaporator" (Abstract).

SUMMARY OF THE INVENTION

The following presents a simplified summary of the invention in order to provide a basic understanding of some of its embodiments. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

The present invention concerns, in a first aspect, a method for making isoidide from an impure isosorbide containing one or more sorbitans ("epimerization reactor feed) mixture comprising impure isosorbide. What is meant by "impure isosorbide" is an isosorbide-rich composition containing one or more sorbitans. In particular embodiments, the isosorbide feedstock containing sorbitans is a minimally purified isosorbide reaction product which is then subjected to epimerization (isomerization). The use of isosorbide feedstock containing sorbitans for isosorbide epimerization is beneficial because of cost savings inherent in less rigorous purification than that required for higher purity isosorbide.

DETAILED DESCRIPTION OF THE INVENTION

Figure 1:
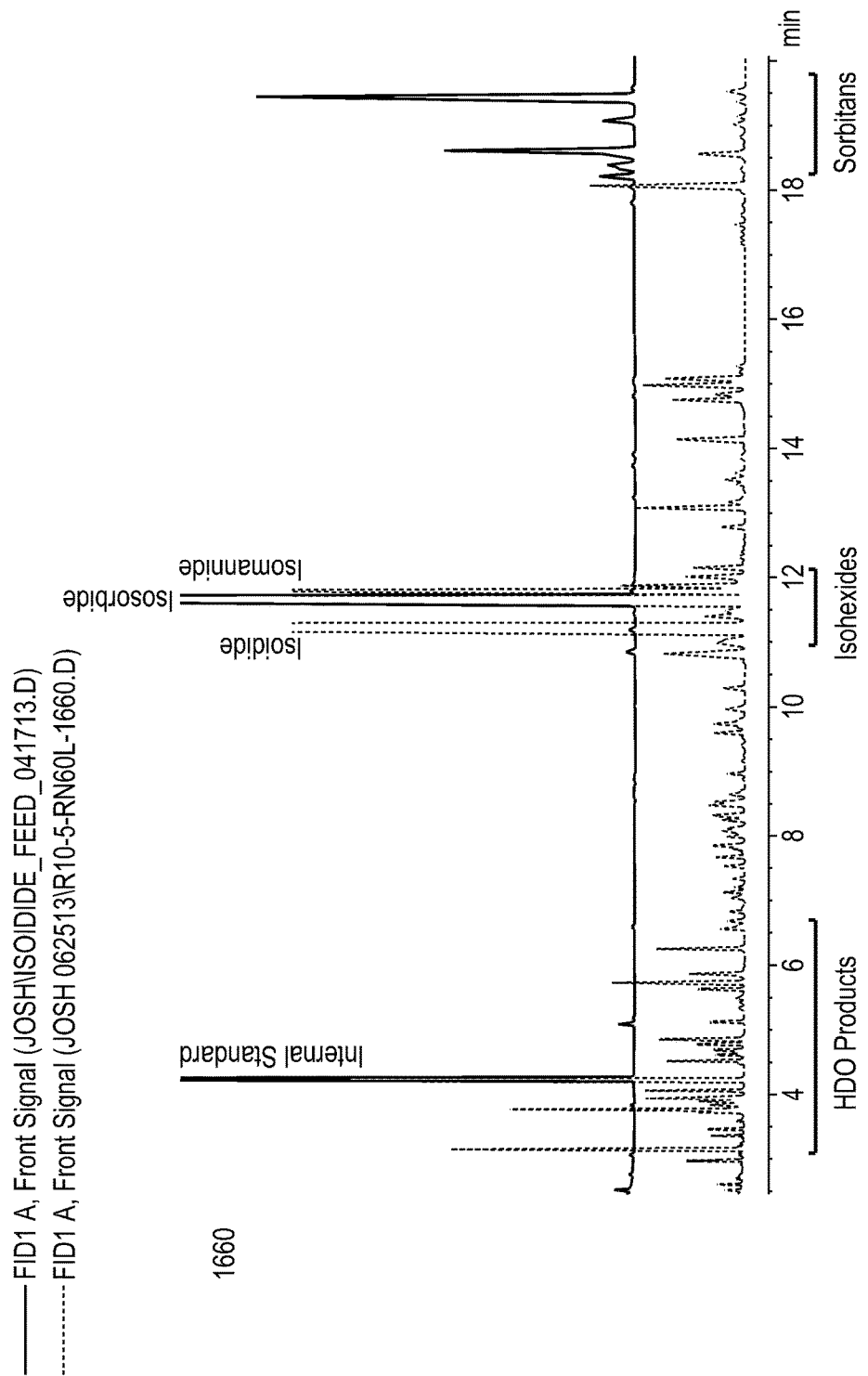
FIG. 1 is a stack plot of GC chromatograms of an isosorbide feedstock containing one or more sorbitans (isoidide reactor feed) and an isoidide reaction product comprising isoidide and hydrodeoxygenation products (generated at 1660 hours).

The present invention relates to a method for making isoidide by epimerizing an incompletely purified isosorbide comprising isosorbide and one or more sorbitans; epimerizing the incompletely purified isosorbide forms an epimerization product comprising isoidide and hydrodeoxygenation products. In an embodiment, providing an isosorbide comprising isosorbide and one or more sorbitans comprises carrying out incomplete purification of an isosorbide containing one or more sorbitans, wherein the impurities comprise by-products generated in the production of isosorbide. In certain embodiments, the providing an isosorbide comprising isosorbide and sorbitans comprises recycling sorbitan-containing, isosorbide rich distillation bottoms from conventional distillative isosorbide manufacturing.

The isosorbide comprising isosorbide and one or more sorbitans may be obtained by dehydrating sorbitol to form an isosorbide product and subjecting the isosorbide product to incomplete purification to provide an isosorbide which contains sorbitans. In certain embodiments the isosorbide comprising isosorbide and one or more sorbitans comprises intermediate process streams in a process for producing at least a technical grade isosorbide product through the dehydration of sorbitol. What is meant by "intermediate process streams in a process for producing at least a technical grade isosorbide product through the dehydration of sorbitol" is any source of material or combination of sources of material found in a process for making isosorbide that contains isosorbide, sorbitans or both. What is meant by "technical grade isosorbide" is a composition containing at least 80% isosorbide. The use of isosorbides, such as these intermediate process streams, as starting materials in isoidide synthesis can result in cost saving due to elimination of isosorbide purification steps.

The impurities in isosorbide feedstock may comprise one or more sorbitans and isomers thereof, such as 1,4-sorbitan monoanhydrohexitol (1,4-anhydrosorbitol), 2,5-anhydrosorbitol, 1,5-anhydrosorbitol and 1,4,3,6-dianhydrosorbitol. In an embodiment, the amount of sorbitans may be greater than 0.1%, greater than 0.2%, greater than 0.5%, greater than 1%, greater than 2%, greater than 3%, greater than 4%, greater than 5%, greater than 6%, greater than 7%, greater than 8%, greater than 9%, greater than 10%, and up to 20% sorbitans.

A method according to the present invention for epimerizing an isosorbide feedstock containing one or more sorbitans to isoidide involves carrying out the synthetic steps for the preparation of an isosorbide composition from sorbitol by acid-catalyzed dehydration as outlined herein and in WO 2014070371, and subjecting the isosorbide composition to incomplete purification by one or perhaps a combination of certain purification steps as outlined herein and in WO 2014070371 A1, but excluding distillation, to generate an isosorbide feedstock comprising one or more sorbitans; the purification steps may be one or more of ultrafiltration, nanofiltration, ion exclusion chromatography, ion exchange chromatography, simulated moving bed chromatography (SMB), and contacting with activated carbon. Compositions subjected to one or more of these steps, but not subjected to distillation temperatures, are considered as compositions which have undergone incomplete purification according to the present invention and thus suited for use as or in an epimerization feedstock according to the inventive process.

Thus, the present invention relates to a method for making isoidide from an isosorbide feedstock which has been subjected to less rigorous purification than is needed for monomer grade isosorbide; the incompleteness of purification is indicated by the presence of sorbitans in the isosorbide. The incompletely purified isosorbide containing one or more sorbitans is not subjected to isosorbide distillation temperatures. By carrying out incomplete purification without subjecting the isosorbide composition to distillation temperatures, substantial cost savings can be achieved; in addition, the heat-sensitive isosorbide can be spared the damaging effects of high temperatures.

Isosorbide containing one or more sorbitans comprises the product obtained by subjecting an isosorbide composition produced from sorbitol by acid-catalyzed dehydration (which isosorbide composition contains sorbitan by-products) to at least one of the following purification steps, to provide the isosorbide containing one or more sorbitans:

Ultrafiltration
Ion exclusion
Ion exchange
Carbon or resin bed adsorption step.

The incomplete purification of isosorbide is carried out as follows: first, ultrafiltration or nanofiltration of the sorbitan-containing isosorbide composition produced from sorbitol by acid-catalyzed dehydration is carried out to reduce the content of molecules larger than the isohexides and sorbitans, such as higher molecular weight, oligomeric or polymeric impurities in the crude dehydration product mixture that may precipitate out and foul subsequent ion exchange and/or ion exclusion resins. Membranes having a molecular weight cut-off of about 1,000 to 10,000 are satisfactory, though those skilled in the art will appreciate that for other crude isohexide product mixtures produced by different methods or under different conditions, other nanofiltration or ultrafiltration membranes may be best or may not be economically worthwhile to implement at all. Examples of the membranes we have tried and found useful under our particular conditions include GE Power™ and Water GE™-series, and PW™-series polyethersulfone ultrafiltration membranes, Sepro™ PES5, PES10 polyethersulfone, and PVDF4™ polyvinylidine fluoride ultrafiltration membranes. The resulting ultrafiltered or nanofiltered process stream obtained is an example of an intermediate process stream in a process for producing at least a technical grade isosorbide product through the dehydration of sorbitol.

Following the nanofiltration or ultrafiltration step, an ion exclusion step is employed for at least partially removing ionic species from the filtered isosorbide product. Preferred ion exclusion resins are chromatographic grade, gel type resins with a volume median diameter between 290-317 µm, where more than 80% of the particle size range is between 280-343 µm and more than 60% of the particle size range is between 294-392 µm, which are characterized by a crosslink density of less than 12%, more preferably less than 8% and ideally less than 6%, and which are in the cation form corresponding to the highest concentration cation present in the crude isosorbide product mixture. The ion exclusion step may be conducted in a batchwise, semibatch or continuous manner and may be conducted through a fixed bed arrangement or a continuous simulated moving bed system. Ion exclusion is carried out with strong acid cation exchange resins in the sodium form; the calcium form is not suitable if the reaction is run with sulfuric acid as the catalyst and neutralized with sodium hydroxide. The resulting ion excluded process stream obtained is an example of an intermediate process stream in a process for producing at least a technical grade isosorbide product through the dehydration of sorbitol.

The ion exclusion step is followed by an ion exchange step for removing additional ionic impurities from the isosorbide, through the use of preferably a fixed bed arrangement including at least one highly crosslinked strong acid cation exchange resin in the hydrogen form and one macroporous, highly crosslinked strong base anion exchange resin in the hydroxide form. As with the materials used for the ion exclusion step, while particular examples follow hereafter, various resins of the indicated types are commercially available and known to those skilled in the art, and it will be well within the capabilities of those of ordinary skill in the use of such ion exchange resins to select and use appropriate resins effectively in the ion exchange step to remove additional impurities of the types listed above from the crude isosorbide composition. The resulting ion exchanged process stream obtained is an example of an intermediate process stream in a process for producing at least a technical grade isosorbide product through the dehydration of sorbitol.

Following ion exchange, the isosorbide may be subjected to a carbon or resin bed adsorption step in an embodiment, principally to remove further nonionic oligomeric and polymeric impurities and/or color bodies that may remain. Preferably a fixed bed arrangement with one or more activated carbons is used. Suitable activated carbons include but are not limited to Norit™ SA2 steam activated carbon from peat, Calgon CPG™-LF low acid soluble iron content granular activated carbon from coal, Calgon CAL™ coal-based granular activated carbon, Nuchar™ SN chemically activated, wood-based powdered activated carbon, Norit™ RO 0.8 high surface area pelletized activated carbon, Nuchar™ WV-B low density, high surface area granular activated carbon, Calgon PCB™ activated carbon from coconut shells, Calgon BL™ powdered, reagglomerated coal-based activated carbon, Nuchar™ RGC high activity, low ash, low soluble iron granular activated carbon, and Nuchar™ SA-20 chemically activated, wood-based powdered activated carbon. Suitable adsorptive resins include but are not limited to macroporous styrene-divinylbenzene type resins, for example, Dowex Optipore™ L493 and Dowex Optipore SD-2™ resins. The resulting process stream obtained is an example of an intermediate process stream in a process for producing at least a technical grade isosorbide product through the dehydration of sorbitol.

In addition, isosorbide containing one or more sorbitans comprises intermediate process streams including one or more of: recycled distillation bottoms from conventional isosorbide manufacturing by distillation as defined at [0043] of US2015126599 (WO2014070371); isosorbide crude reaction mixture neutralized as defined at [0077] of US2015126599 (diluted with deionized water and filtered through a 0.2 pm filter, containing 46.025 wt. % of isosorbide, 7.352 wt. pct. of sorbitans, and 34.940 wt. pct. of water; extracts from a series of simulated moving bed ion exclusion isosorbide purification steps as defined at [0080] of US2015126599 containing 29.45 percent by weight of isosorbide, 3.31 weight percent of sorbitans, and 67.14 percent by weight of water; combined ion-excluded, ion-exchanged isosorbide mixture as defined at [0080] of US2015126599 containing 72.20 wt percent isosorbide, 8.12 wt percent sorbitans, 5.63 wt percent of water; or degassed isosorbide residue as defined at [0083] of US2015126599 containing 83.81 percent by weight of isosorbide, 0.19 percent by weight of isomannide, 0.07 percent by weight of isoidide, and 12.22 percent by weight of sorbitans. Process stream such as isosorbide and sorbitan containing streams from companion patent applications are also suitable. Sources for intermediate process streams containing isosorbide and sorbitols include the process streams of patent applications and publication nos. WO2013125950, WO2014070369, WO2014070370, WO 2014070371, WO2014137619, WO2015112389, WO2015156846 A1, WO2015166070 A1, and US2015126599; those skilled will recognize in contemplation of these processes that any stream or source or intermediate of the process containing isosorbide and sorbitans can be used as the isosorbide source for an intermediate process stream. Each of these is an example of an intermediate process stream in a process for producing at least a technical grade isosorbide product through the dehydration of sorbitol. The skilled artisan will recognize that these process streams will be attractive in the case of implementing isoidide manufacture in existing isosorbide manufacturing plants ("Brownfield"), as well as in the case of "Greenfield" new construction of a dedicated isoidide manufacturing plant.

Isosorbide containing one or more sorbitans may be obtained by adding sorbitans to the one or more intermediate process streams or to one or more commercially available isosorbides.

At any point before, during, or after being subjected to one or more of the steps of ultrafiltration, nanofiltration, ion exclusion chromatography, ion exchange chromatography, and/or contacting with activated carbon, the water content of the isosorbide composition may be adjusted, such as by evaporation or adding water. Unlike the more conventional methods of isosorbide purification designed to produce a commercial or USP grade of isosorbide, such as distillation, these incomplete purification processes are operated without subjecting the isosorbide to distillation temperatures, such as by operating at or near ambient temperature. The boiling point of isosorbide under vacuum reported ranges from 152-165° C. under 400-1333 pascal vacuum. The range of temperatures at which the purification processes are operated without subjecting the isosorbide to distillation temperatures can easily be determined by the person having average skill in the art. By carrying out purification without subjecting the isosorbide composition to distillation temperatures, substantial cost savings can be achieved; in addition, the heat-sensitive isosorbide can be spared the damaging effects of high temperatures.

A composition comprising isosorbide containing one or more sorbitans may comprise a commercially available isosorbide. These are available in a range of purities, including POLYSORB™ pure isosorbide for polymers such as polycarbonates & polyesters (99.5% minimum purity, from Roquette, 62080 Lestrem cedex, France); ≥99% pure isosorbide (TCI Fine Chemicals, Portland, Oreg.); POLYSORB PB/LPB™ technical isosorbide for intermediates and isosorbide derivatives (98% minimum purity, from Roquette); 95-98% purity (Alfa Aeser, Ward Hill, Mass.), and 90-95% purity (eNovation Chemicals LLC, Bridgeport, N.J.).

The isosorbide feedstock containing one or more sorbitans can be characterized by a ratio of the total content of isohexides to the total content of sorbitans. In an example below, the ratio of isohexide content to sorbitan content (in weight percent) in the isosorbide comprising sorbitans subjected to epimerization in example 5 from hour 1868 to 2701 was 8.06 (44.9% total isohexides, 5.57% total sorbitans); the ratio in the incompletely purified isosorbide ("isosorbide feedstock containing one or more sorbitans) mixture subjected to epimerization from hour 2741 to 2701 was 9.39 (41.3% total isohexides, 4.40% total sorbitans). Incompletely purified isosorbide feedstock (isosorbide feedstock containing one or more sorbitans) includes isosorbide compositions in which the ratio of isohexide content to sorbitan content (in weight percent) ranges from one to two hundred, including the endpoints and the entire range, i.e., ranging from 50% isohexide/50% sorbitans to 99.5% isohexides/ 0.5% sorbitans where the content in weight percent of isohexides and sorbitans in the composition is normalized to 100%. Exemplary ratios of the content of isohexide to the content of sorbitan in the isosorbide feedstock containing one or more sorbitans include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 and fractions thereof.

The relative amounts of isohexide and sorbitans in the incompletely purified isosorbide feedstock may be expressed in terms of weight percent isohexides/weight percent sorbitans (where the content in weight percent of isohexides and sorbitans in the composition is normalized to 100% and any water or other solvent present is not included), and may include ratios of 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.5/0.5, and fractions thereof.

After an isosorbide containing one or more sorbitans is obtained by any of the above methods, it is subjected to epimerization wherein the isosorbide is epimerized, forming an epimerization product comprising isoidide and hydrodeoxygenation products. In certain embodiments, the epimerization is carried out according to WO 2013/125950 A1 to Hagberg et al. Therein, an aqueous solution of isosorbide is subjected to epimerization in the presence of hydrogen under the influence of a catalyst comprising ruthenium on a support, at a starting pH of above 7. WO'950 further provides a process for the preparation of isoidide from glucose by hydrogenating glucose to form sorbitol, dehydrating the resulting sorbitol to form isosorbide, then epimerizing the isosorbide into isoidide using a catalyst comprising carbon-supported ruthenium at a pH above 7. Alternatively, the process of Wright and Brandner, J. Org. Chem., 1964, 29 (10), pp 2979-2982 can be used to make isoidide. They taught epimerization by means of Ni catalysis, using nickel supported on diatomaceous earth. The reaction was conducted under relatively severe conditions, such as a temperature of 220° C. to 240° C. at a pressure of 150 atmosphere. The reaction reached a steady state after two hours, with an equilibrium mixture containing isoidide (57%), isosorbide (36%) and isomannide (7%). Comparable results were obtained when starting from isoidide or isomannide. Increasing the pH to 10-11 was found to have an accelerating effect, as well as increasing the temperature and nickel catalyst concentration. A similar disclosure is to be found in U.S. Pat. No. 3,023,223.

Surprisingly, in certain embodiments, isoidide can be synthesized from an incompletely purified isosorbide composition. Isohexide mass losses can be accounted for in "mass loss" of isohexides or "decomposition" of isohexides. HDO products may correspond to "mass loss" of sorbitans, "decomposition" of sorbitans, "mass loss" of isohexides, or "decomposition" of isohexides. At least some of the mass loss is due to the formation of hydrodeoxygenation (HDO) products, which may be formed from isohexides or sorbitans. HDO products were defined as compounds in the chromatogram between 3 and 6.75 minutes (FIG. 1).

Without wishing to be bound by theory, it is believed that the sorbitans decompose in the epimerization reactor to form compounds having boiling points below the boiling point of the desired isoidide. These include hydrodexygenation (HDO) products; HDO products have been characterized as a mixture of straight chain aliphatic alcohols with low boiling points relative to isohexides (volatiles: propanols, butanols, hexanols, alkanes; nonvolatiles: propanediols, butanediols, hexanediols, furanol; (supporting information for LeNotre et al., ChemSusChem 6, 693-700 2013 at http://onlinelibrary.wiley.com/store/10.1002/cssc.201200714/asset/supinfo/cssc_201200714_sm_miscellaneous_information.pdf?v=1&s=89d9ec835660174ab84c20ed377959f2d1e0a55c accessed Nov. 19, 2014).

FIG. 1 shows a GC/FID stack plot of chromatograms of the incompletely purified isosorbide composition comprising sorbitans and the subsequent epimerization reaction product generated at 1660 hours. The nearly complete elimination of sorbitans present in the feed to the reactor resulted in an isoidide product with a very low content of sorbitans. Hydrodeoxygenation products increased to about 25%.

In certain embodiments, epimerization is carried out by forming an isosorbide comprising isosorbide and sorbitans and epimerizing the isosorbide in the presence of hydrogen and an epimerization catalyst selected from the group consisting of nickel supported on diatomaceous earth, a supported nickel hydrogenation catalyst, Raney nickel, ruthenium on carbon, ruthenium on a support, ruthenium on aluminum oxide, palladium on carbon, platinum on carbon, rhodium on carbon, gold on carbon, nickel on silica dioxide, and palladium hydroxide on carbon (Pearlman's catalyst), and combinations of any thereof to form the epimerization product comprising isoidide and hydrodeoxygenation products.

In a further embodiment, the yield of isoidide produced in epimerization of isosorbide ranges from 27-58 wt %; wherein the yield is defined as the amount of isoidide relative to the sum of the amounts isoidide, isosorbide, and isomannide; and wherein the amounts are determined using a DB-5 MS UI column (30 m×0.25 mm×0.25 um) on a gas chromatograph equipped with an FID detector.

In yet another embodiment, the yield of isoidide, is at least 27 wt. %, is at least 28 wt. %, is at least 29 wt. %, is at least 30 wt. %, is at least 31 wt. %, is at least 32 wt. %, is at least 33 wt. %, is at least 34 wt. %, is at least 35 wt. %, is at least 36 wt. %, is at least 37 wt. %, is at least 38 wt. %, is at least 39 wt. %, is at least 40 wt. %, is at least 41 wt. %, is at least 42 wt. %, is at least 43 wt. %, is at least 44 wt. %, is at least 45 wt. %, is at least 46 wt. %, is at least 47 wt. %, is at least 48 wt. %, is at least 49 wt. %, is at least 50 wt. %, is at least 51 wt. %, is at least 52 wt. %, is at least 53 wt. %, is at least 54 wt. %, is at least 55 wt. %, is at least 56 wt. %, is at least 57 wt. %, is at least 58 wt. %.

The epimerization reaction brings about a reduction in the content of sorbitans in the isosorbide feedstock containing one or more sorbitans. Consequently the content of sorbitans in the isosorbide feedstock containing one or more sorbitans is greater than the content of sorbitans in the epimerization reactor product comprising isoidide.

Particularly, the epimerization of an isosorbide feedstock containing one or more sorbitans may be carried out over nickel at a pressure of 2000 psi (13.79 MPa), a hydrogen flow of 1000 mL/minute, reaction temperature of 225-235° C., and at a liquid hourly space velocity of 1/hr.

The epimerization reaction results in an epimerization product comprising isoidide, other isohexides, and ionic species. At least partially removing ionic species from an epimerization product comprising isoidide permits a chromatographic separation of isoidide from other isohexides, resulting in a stream enriched in isoidide and a stream enriched in the other isohexides.

The epimerization product comprising isoidide, other isohexides (isosorbide and isomannide) and ionic species (such as ions resulting from adjusting the pH of the epimerization reactor feed to 10, and acidic HDO products) is prepared for chromatographic separation of isoidide from other isohexides by at least partially removing ionic species. Ions are at least partially removed from epimerization product comprising isoidide and other isohexides by contacting with cation exchange resin in the proton form and anion exchange resin in the hydroxyl form. Typical products removed by the contacting include sodium ions and acid HDO by-products of epimerization. Ionic species may be removed to below detection limits as determined by inductively coupled plasma atomic emission spectroscopy (ICP); the limit of detection of sodium in this matrix as 0.01 ppm. Subsequently, dewatering, such as by rotary evaporation, may be carried out to adjust the water content to the desired level.

Following the at least partial removal of ionic species, chromatographic separation of isoidide from other isohexides is carried out. What is meant by "chromatographic separation" and variations thereof refers to rate-based separation of chemical species over a stationary solid phase chromatographic sorbent material by differential partitioning of the species between the stationary phase and a mobile eluent phase. What is meant by "chromatographic separation of isoidide from other isohexides" and variations thereof refers to rate-based separation of chemical species over a stationary solid phase chromatographic sorbent material by differences in the, on the one hand, partitioning of the isoidide between the stationary phase and a mobile eluent phase, and, on the other hand, partitioning of other isohexides between the stationary phase and a mobile eluent phase. Typical "other isohexides" include, but are not limited to, isosorbide and isomannide. By "rate based separation" it is meant that a portion of each species is always moving with the mobile phase eluent but that a difference in partitioning rates between species results in a different rate of movement of species over the stationary phase thereby accomplishing a separation dependent on time and bed volume. Accordingly, chromatographic separation can be accomplished by the use of single mobile phase without a requirement to change eluent conditions. In this regard, chromatographic separation may be characterized as a "continuous separation process" because the species being separated are in continuous motion.

Figure 2:
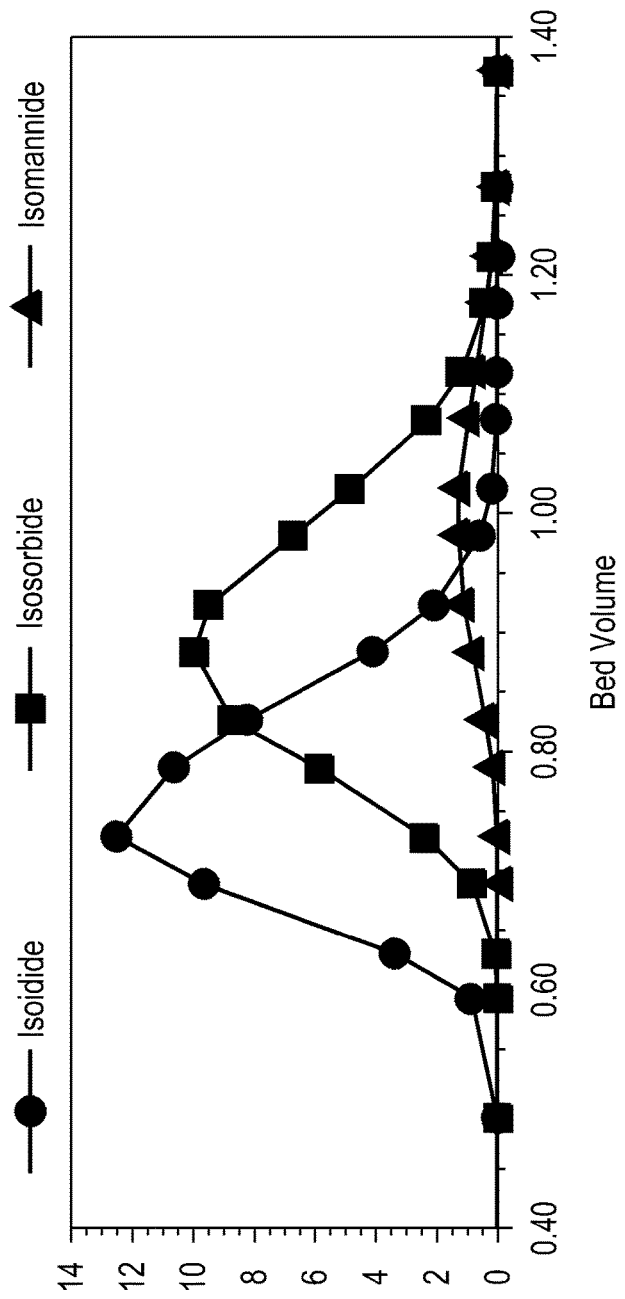
FIG. 2 depicts the elution profile of a pulse test for the separation of isoidide, isosorbide, and isomannide from Example 6 using Diaion UBK530™ ion exchange resin (BV=flow*step time/column volume).

With this in mind, the present invention additionally in part relates to the discovery that isoidide can be chromatographically purified using ion exchange resins, particularly strong acid ion exchange resins in the Ca $2^+$ form. The selectivity of the ion exchange resins can be determined by contacting the resin with a composition comprising isosorbide reaction product (impure isosorbide comprising one or more sorbitans) containing by-products of the epimerization of isosorbide. A single-column discontinuous preliminary test used in the art of simulated moving bed chromatography to identify suitable chromatographic conditions for purification of desired compounds may be carried out. One suitable name for such a test is a "Pulse Test". A fraction collector is suitable for obtaining fractions of the effluent which may be analyzed to determine the effectiveness of resin in separating the feed into fractions selectively enriched in compounds contained in the feed. The concentrations of the compounds in the fractions can then be plotted as in FIG. 2 to provide guidance in optimizing the operational conditions in subsequent simulated moving bed separation.

The capacity (Retention Factor and Relative Retention) of the strong acid ion exchange resins in the Ca $2^+$ form is calculated by the following equation:

$$\text{Capacity}(k)=(tr-t0)/t0$$

tr=retention time (or volume) of peak
t0=retention time (or volume) of unretained peak or void volume, either measured or taken from resin porosity data The selectivity of the strong acid ion exchange resins in the Ca $2^+$ form is calculated by the following equation:

$$\text{Selectivity}(\alpha)=k2/k1$$

k2=retention factor of the late eluting peak
k1=retention factor of early eluting peak
Thus, the coefficient of selectivity (a, alpha) (also referred to herein as "selectivity") of a resin is the ratio of the retention factors of two peaks.

The efficiency of the strong acid ion exchange resins in the Ca $2^+$ form is calculated by the following equation:

$$\text{Efficiency}(N)=5.54(tR/W)^2$$

tR=Retention time of peak of interest
W=Width of peak of interest at half height With respect to resins, in certain embodiments, strong acid ion exchange resins in the calcium $2^+$ form can be selected. In preferred embodiments, resins may be selected from the group consisting of Diaion PK-216™, Diaion SK-104™, Diaion SK-110™, Diaion SK-112™, Diaion UBK-530™, Diaion UBK-555™, from Mitsubishi Chemical Corp. (New York, N.Y.); Dow-99-310™ (Dow Chemical Co. (Midland, Mich.); Lewatit MDS 1368™ from Lanxess (Burmingham, N.J.); Purolite PCR-631™, Purolite PCR-642™, Purolite PCR-855™ from Purolite Co. (Bala Cynwyd, Pa.); and Tulsion T-38™ from Thermax, Inc. (Novi, Mich.), and combinations of any thereof.

The present method of chromatographically separating the isoidide from other isohexides to obtain a stream enriched in isoidide and a stream enriched in the other isohexides utilizes simulated moving bed chromatography. Several chromatographic beds, columns or parts thereof are aligned in a series wherein a feed flows through any number of chromatographic devices. An arrangement of valves at the top and bottom of each column direct the flow of eluents and products to subsequent columns in the same or a different zone. In this manner, the continuous movement of bed material is simulated. Thus, "zones" are defined not by the physical columns but by the function each column carries out at a given time. In a complete cycle, each column has passed through each zone in the same sequence and continues. Feed and eluent can be applied at any column, and compound (s) to elute can be passed out from the series at any column through an outlet in an effluent stream. One of ordinary skill in the art can adjust parameters such as feed rate of the feed, eluent flow rate, reload rate and step time to improve the separation.

In the present enrichment method, the simulated moving bed chromatography (SMB) can comprise one or more zones. A zone is defined by the primary function of the chromatographic beds, columns or parts thereof. In a preferred embodiment, the present method utilizes four zones, wherein each zone comprises one or more chromatographic devices. In certain embodiments, one or more of the described zones can be replaced or eliminated. In other embodiments, one or more zone can be duplicated and operated sequentially with the other zones. In an embodiment, the zones comprise a third (feed/raffinate) zone, a fourth (reload) zone, a first (eluent/extract) zone, and a second (enrichment) zone.

In an embodiment, the at least partially deionized epimerization product comprising isoidide and other isohexides is applied continuously to the third (feed/raffinate) zone and contacted with a resin comprising at least one strong acid ion exchange resin in the cation form. A raffinate comprising an isoidide enriched composition containing a greater proportion of isoidide than the epimerization product and having a reduced level of isosorbide or isomannide is continuously eluted from the SMB in this zone and allowed to pass out of the SMB as an effluent labeled "Raffinate."

A further embodiment comprises chromatography operating parameters yielding the greatest proportion of isoidide in the sum of isoidide plus any isosorbide present plus any isomannide present in the isoidide enriched composition. What is meant by "isoidide enriched composition" is a composition comprising isoidide and containing a proportion of isoidide in the sum of isoidide plus isosorbide plus isomannide which, when compared to an impure isoidide composition, contains a greater proportion of isoidide. What is meant by isoidide plus isosorbide plus isomannide is isoidide plus any isosorbide present plus any isomannide present. The proportion of isoidide in the isoidide enriched composition may be greater than or equal to any of 40, 45, 50, 55, 60, 65, 70, 75, 80, 85, 85, 87, 88, 89, 90, 91, 92, 93, 94, 95, 96, 97, 98, or 99 parts out of 100 parts (weight/weight). In a desired embodiment, the proportion of isoidide in the sum of isoidide plus isosorbide plus isomannide of the isoidide enriched composition is desirably greater than or equal to 80 parts out of 100 parts (weight/weight).

An alternative description of "isoidide enriched composition" is a composition comprising isoidide and isosorbide and/or isomannide in which the ratio of the weight percent of isoidide to the weight percent of isosorbide and/or isomannide is greater than the ratio of the weight percent of isoidide to the weight percent of isosorbide and/or isomannide in a corresponding starting material or feed, such as an impure isoidide composition, without including water or other solvent. Exemplary ratios of weight percent of isoidide to weight percent of isosorbide and/or isomannide in an isoidide enriched composition include 1.01, 1.02, 1.03, 1.04, 1.05, 1.06, 1.07, 1.08, 1.09, 1.1, 1.125, 1.15, 1.175, 1.2, 1.225, 1.25, 1.275, 1.3, 1.325, 1.35, 1.375, 1.4, 1.425, 1.45, 1.475, 1.5, 1.525, 1.55, 1.575, 1.6, 1.625, 1.65, 1.675, 1.7, 1.725 1.75, 1.775, 1.8, 1.825, 1.85, 1.875, 1.9, 1.925, 1.95, 1.975, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.25, 5.5, 5.75, 6.0, 6.25, 6.5, 6.75, 7.0, 7.2.5, 7.5, 7.75, 8.0, 8.25, 8.5, 8.75, 9.0, 9.25, 9.5, 9.75, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40, 41, 42, 43, 44, 45, 46, 47, 48, 49, 50, 55, 60, 65, 70, 75, 80, 85, 90, 95, 100 and fractions of any thereof. In a preferred embodiment, the weight ratio of isoidide to isosorbide+isomannide in an isoidide enriched composition (raffinate) ranges from 1.1 to 19.0.

The resin bed passes into the second (enrichment) zone, in which the isosorbide and isomannide on the bed are enriched in the subsequent extract. The resin bed passes into the first (eluent/extract) zone, in which water eluent is applied and an extract enriched in isosorbide/isomannide (having a higher ratio of isosorbide and/or isomannide to isoidide than the first ratio of isosorbide and/or isomannide to isoidide in the feed) is continuously eluted as an effluent labeled "Extract."

The number of chromatographic beds, columns or parts thereof contained in the series can be unlimited. The present method can be optimized using the parameters stated above to improve product yield. Within the series of chromatographic devices, there are one or more zones as described above. Each zone contains an independent number of chromatographic devices. The preferred embodiment is not limited to any number of chromatographic devices because the method is scalable, wherein the process parameters are readily scalable by one of ordinary skill in the art. One of the parameters is the unlimited number of chromatographic devices in a series and the number within each zone in the series.

SMB chromatography is a robust tool that can be altered in an optimization process to achieve the desired objectives. In one embodiment, the optimization process may target improvements in resin usage, where higher resin usage is desired. A further embodiment of the optimization is obtaining the highest yield of one or more components undergoing separation. Dilution of the desired compounds often occurs in simulated moving bed chromatography, and another embodiment of the optimization process is lowering the dilution of one or more desired compounds. Yet another embodiment of optimization comprises obtaining the desired proportions of components, such as isoidide/isosorbide/isomannide, in the product (extract) or raffinate. The proportions can be characterized by ratios of weight percents of one component to the weight percents of another component, or by ratios of weight percents of one component to the weight percents of the other components.

In development of various embodiments of the optimization of SMB chromatography the flow rate of each stream and zone may be adjusted, including the eluent, the feed, the raffinate, the product (extract), each zone in the SMB, and the resin. In the non-limiting examples below, four zones are used, so a total of nine flow rates are adjustable in pursuit of various embodiments. The flow rates of liquid streams are adjustable by changing pump speeds, and the flow rate of the resin is adjustable by changing the step time. SMB chromatography operating parameters can be adjusted to provide the highest resin usage. Alternatively, the SMB chromatography operating parameters can be adjusted to obtain the highest yield of isoidide in the raffinate. Yet another alternative comprises operating within parameters producing the highest concentration of isoidide (the lowest level of dilution) in the raffinate.

A stream enriched in isoidide obtained by SMB containing solvent, such as water, and impurities that are more volatile than isoidide, such as hydrodeoxygenation products, may be subjected to distillation to remove solvent and/or impurities and obtained more concentrated isoidide streams. Streams enriched in isoidide containing about 5-20% water provide desirable crystallization characteristics. Conventional distillation techniques, such as short path distillation, maybe employed; evaporators such as wiped film evaporators or thin film evaporators are also suitable to concentrate the isoidide before crystallization. From the standpoint of minimizing the heat exposure of isoidide, removing water solvent may be carried out at a temperature of 70 degrees C. or less.

In an embodiment, a method is provided for synthesizing isoidide, the method comprising providing an isosorbide containing one or more sorbitans, and epimerizing the isosorbide to form an epimerization product comprising isoidide and hydrodeoxygenation products. In an alternative embodiment, the isosorbide containing one or more sorbitans is obtained from one or more intermediate process streams in a process for producing at least a technical grade isosorbide product through the dehydration of sorbitol, or from adding sorbitans to a technical grade or better isosorbide. In a further embodiment, the isosorbide containing one or more sorbitans is obtained by adding one or more sorbitans to one or more intermediate process streams containing isosorbide, or by adding additional of the one or more sorbitans to one or more intermediate process streams containing both isosorbide and one or more sorbitans. In yet another embodiment, the isosorbide containing one or more sorbitans is obtained from one or more of incompletely purified isosorbide, partially purified isosorbide, intermediately purified isosorbide streams, recycled distillation bottoms from isosorbide manufacturing, isosorbide crude reaction mixture, extracts from a series of simulated moving bed ion exclusion isosorbide purification steps, combined ion-excluded, ion-exchanged isosorbide mixtures, degassed isosorbide residue, commercially available isosorbide and combinations of any thereof.

In another alternative embodiment, epimerization is carried out in the presence of hydrogen and an epimerization catalyst selected from the group consisting of nickel supported on diatomaceous earth, a supported nickel hydrogenation catalyst, Raney nickel, ruthenium on carbon, ruthenium on a support, ruthenium on aluminum oxide, palladium on carbon, platinum on carbon, rhodium on carbon, gold on carbon, nickel on silica dioxide, palladium hydroxide on carbon, Pearlman's catalyst, and combinations of any thereof to form the epimerization product comprising isoidide and hydrodeoxygenation products. In another embodiment, an intermediate process stream or streams is/are selected, one or more sorbitans may be added thereto, or sufficient sorbitans are added to a technical grade or better isosorbide, such that the amount of sorbitans in the resultant isosorbide is greater than 0.1%, greater than 0.2%, greater than 0.5%, greater than 1%, greater than 2%, greater than 3%, greater than 4%, greater than 5%, greater than 6%, greater than 7%, greater than 8%, greater than 9%, greater than 10% and up to 20% sorbitans. In an alternative embodiment, the ratio of isohexide content to sorbitan content (in weight percent) in the isosorbide ranges from one to two hundred.

In a still further embodiment, the yield of isoidide produced in epimerization of isosorbide ranges from 27-58 wt %; the yield is defined as the amount of isoidide relative to the sum of the amounts isoidide, isosorbide, and isomannide; the amounts are determined using a DB-5 MS UI column (30 m×0.25 mm×0.25 um) on a gas chromatograph equipped with an FID detector. In selected embodiments, the yield of isoidide, is at least 27 wt. %, is at least 28 wt. %, is at least 29 wt. %, is at least 30 wt. %, is at least 31 wt. %, is at least 32 wt. %, is at least 33 wt. %, is at least 34 wt. %, is at least 35 wt. %, is at least 36 wt. %, is at least 37 wt. %, is at least 38 wt. %, is at least 39 wt. %, is at least 40 wt. %, is at least 41 wt. %, is at least 42 wt. %, is at least 43 wt. %, is at least 44 wt. %, is at least 45 wt. %, is at least 46 wt. %, is at least 47 wt. %, is at least 48 wt. %, is at least 49 wt. %, is at least 50 wt. %, is at least 51 wt. %, is at least 52 wt. %, is at least 53 wt. %, is at least 54 wt. %, is at least 55 wt. %, is at least 56 wt. %, is at least 57 wt. %, is at least 58 wt. %.

In an alternative embodiment, the content of sorbitans in the isosorbide feedstock containing one or more sorbitans is greater than the content of sorbitans in the epimerization reactor product comprising isoidide. In another selected embodiment, the epimerization of an isosorbide containing one or more sorbitans is carried out over nickel at a pressure of about 2000 psi (13.79 MPa), a hydrogen flow of about 1000 mL/minute, reaction temperature of 225-235° C., and at a liquid hourly space velocity of about 1/hr. In yet another embodiment, a composition is provided comprising isoidide synthesized according to any of the embodiments provided herein.

In an embodiment, a method of preparing an isoidide enriched composition comprising is presented, the method comprising at least partially removing ionic species from an epimerization product comprising isoidide to obtain an at least partially deionized isoidide composition comprising isoidide and other isohexides, and chromatographically separating the isoidide from other isohexides to obtain a stream enriched in isoidide and a stream enriched in the other isohexides.

In another embodiment, the chromatographic separation is carried out by contacting the at least partially deionized isoidide composition with a resin comprising strong acid ion exchange resin in the calcium 2+ form, contacting the at least partially deionized isoidide composition comprising isoidide and other isohexides and the resin with a solvent, and eluting a stream enriched in isoidide and a second stream enriched in the other isohexides. In yet another embodiment, the amount of ions in the at least partially deionized isoidide composition is below detection limits as determined by inductively coupled plasma atomic emission spectroscopy. In still another embodiment, the resin is contained on chromatographic beds, columns or parts thereof arranged in a simulated moving bed chromatographic array. In another embodiment, the solvent comprises water. In yet another embodiment, the stream enriched in isoidide may be subjected to drying; upon drying the stream enriched in isoidide, the proportion of isoidide in the stream enriched in isoidide is greater than 40, 45, 50, 55, 60, 65, 70, 75, 80, 85, 85, 87, 88, 89, 90, 91, 92, 93, 94, 95, 96, 97, 98, or 99 parts out of 100 parts (weight/weight).

In a further embodiment, the stream enriched in isoidide further comprises at least one of isomannide and isosorbide, and (ii) the ratio of isoidide to solvent in the stream enriched in isoidide is greater than the ratio of isoidide to solvent in the at least partially deionized isoidide composition comprising isoidide and other isohexides and/or (iii) the weight ratio of isoidide to isosorbide and/or isomannide in the stream enriched in isoidide is greater than 1.01, 1.02, 1.03, 1.04, 1.05, 1.06, 1.07, 1.08, 1.09, 1.1, 1.125, 1.15, 1.175, 1.2, 1.225, 1.25, 1.275, 1.3, 1.325, 1.35, 1.375, 1.4, 1.425, 1.45, 1.475, 1.5, 1.525, 1.55, 1.575, 1.6, 1.625, 1.65, 1.675, 1.7, 1.725 1.75, 1.775, 1.8, 1.825, 1.85, 1.875, 1.9, 1.925, 1.95, 1.975, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.25, 5.5, 5.75, 6.0, 6.25, 6.5, 6.75, 7.0, 7.2.5, 7.5, 7.75, 8.0, 8.25, 8.5, 8.75, 9.0, 9.25, 9.5, 9.75, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40, 41, 42, 43, 44, 45, 46, 47, 48, 49, 50, 55, 60, 65, 70, 75, 80, 85, 90, 95, or 100.

In an embodiment, the stream enriched in isoidide (raffinate, isoidide enriched composition) is subjected to a crystallization step. In an alternate embodiment, the crystallization is carried out by removing or reducing solvent from the (raffinate) stream enriched in isoidide, and seeding the desolventized stream enriched in isoidide with at least one crystal of isoidide. In an embodiment, the crystallization is carried out in a single stage. In another embodiment, the crystallization selectively enriches isoidide in a crystal phase and selectively enriches isosorbide in a liquid phase. In still another embodiment, the isosorbide-rich liquid phase obtained is subjected to epimerization.

In an embodiment, prior to crystallization the stream enriched in isoidide comprises 5-20% water. In yet another embodiment, removing the solvent from the stream enriched in isoidide is carried out at a temperature of 70° C. or less. In an embodiment, a composition comprising at least one isoidide crystal is obtained wherein the isoidide crystal comprises isoidide obtained by chromatographic separation of isoidide from other isohexides in an at least partially deionized isoidide composition comprising isoidide and other isohexides according to any embodiment herein, preferably wherein the crystals comprise isoidide and water. In a still further embodiment, the level of isosorbide in the crystals is less than 20%.

In another embodiment, "monomer grade isoidide" comprising isoidide crystals containing at least 99.0, at least 99.1, at least 99.2, at least 99.3, at least 99.4, at least 99.5, at least 99.6, at least 99.7, at least 99.8, or at least 99.9 isoidide suitable for use in polymers is obtained. In a preferred embodiment, 100% isoidide suitable for use in polymers is obtained.

The invention can also be defined by the following items:

Item 1. A method for synthesizing isoidide, comprising, providing an isosorbide containing one or more sorbitans; and, epimerizing the isosorbide to form an epimerization product comprising isoidide and hydrodeoxygenation products.

Item 2. The method of item 1, wherein the isosorbide containing one or more sorbitans is obtained from one or more intermediate process streams in a process for producing at least a technical grade isosorbide product through the dehydration of sorbitol, or from adding sorbitans to a technical grade or better isosorbide.

Item 3. The method of item 2, wherein the isosorbide containing one or more sorbitans is obtained by adding one or more sorbitans to one or more intermediate process streams containing isosorbide, or by adding additional of the one or more sorbitans to one or more intermediate process streams containing both isosorbide and one or more sorbitans.

Item 4. The method of items 2 or item 3, wherein the isosorbide containing one or more sorbitans is obtained from one or more of incompletely purified isosorbide, partially purified isosorbide, intermediately purified isosorbide streams, recycled distillation bottoms from isosorbide manufacturing, isosorbide crude reaction mixture, extracts from a series of simulated moving bed ion exclusion isosorbide purification steps, combined ion-excluded, ion-exchanged isosorbide mixtures, degassed isosorbide residue, commercially available isosorbide and combinations of any thereof.

Item 5. The method of any of items 1-4, wherein epimerization is carried out in the presence of hydrogen and an epimerization catalyst selected from the group consisting of nickel supported on diatomaceous earth, a supported nickel hydrogenation catalyst, Raney nickel, ruthenium on carbon, ruthenium on a support, ruthenium on aluminum oxide, palladium on carbon, platinum on carbon, rhodium on carbon, gold on carbon, nickel on silica dioxide, palladium hydroxide on carbon, Pearlman's catalyst, and combinations of any thereof to form the epimerization product comprising isoidide and hydrodeoxygenation products.

Item 6. The method item 5, further comprising selecting an intermediate process stream or streams, selecting an intermediate process stream or streams and adding one or more sorbitans thereto, or adding sufficient sorbitans to a technical grade or better isosorbide, such that the amount of sorbitans in the resultant isosorbide is greater than 0.1%, greater than 0.2%, greater than 0.5%, greater than 1%, greater than 2%, greater than 3%, greater than 4%, greater than 5%, greater than 6%, greater than 7%, greater than 8%, greater than 9%, greater than 10% and up to 20% sorbitans.

Item 7. The method of item 6, wherein the ratio of isohexide content to sorbitan content (in weight percent) in the isosorbide ranges from one to two hundred.

Item 8. The method of item any of items 1-7, wherein the yield of isoidide produced in epimerization of isosorbide ranges from 27-58 wt %; wherein the yield is defined as the amount of isoidide relative to the sum of the amounts isoidide, isosorbide, and isomannide; and wherein the amounts are determined using a DB-5 MS UI column (30 m×0.25 mm×0.25 um) on a gas chromatograph equipped with an FID detector.

Item 9. The method of any of items 1-8, wherein the yield of isoidide, is at least 27 wt. %, is at least 28 wt. %, is at least 29 wt. %, is at least 30 wt. %, is at least 31 wt. %, is at least 32 wt. %, is at least 33 wt. %, is at least 34 wt. %, is at least 35 wt. %, is at least 36 wt. %, is at least 37 wt. %, is at least 38 wt. %, is at least 39 wt. %, is at least 40 wt. %, is at least 41 wt. %, is at least 42 wt. %, is at least 43 wt. %, is at least 44 wt. %, is at least 45 wt. %, is at least 46 wt. %, is at least 47 wt. %, is at least 48 wt. %, is at least 49 wt. %, is at least 50 wt. %, is at least 51 wt. %, is at least 52 wt. %, is at least 53 wt. %, is at least 54 wt. %, is at least 55 wt. %, is at least 56 wt. %, is at least 57 wt. %, is at least 58 wt. %.

Item 10. The method of any of items 1-9, wherein the content of sorbitans in the isosorbide feedstock containing one or more sorbitans is greater than the content of sorbitans in the epimerization reactor product comprising isoidide.

Item 11. The method of any of items 1-10, wherein the epimerization of an isosorbide containing one or more sorbitans is carried out over nickel at a pressure of about 2000 psi (13.79 MPa), a hydrogen flow of about 1000 mL/minute, reaction temperature of 225-235° C., and at a liquid hourly space velocity of about 1/hr.

Item 12. A composition comprising isoidide synthesized according to any of items 1-11.

The present invention is further demonstrated by the examples that follow.

EXAMPLE 1

Crude isosorbide was produced substantially as outlined in International Patent Application No. WO2014070371 by dehydrating sorbitol. Granular crystalline sorbitol (Archer Daniels Midland Co., Decatur Ill.) was melted and heated to an internal temperature of 140° C. under vacuum (<10 Torr; <1333 Pa). Concentrated sulfuric acid was added and the reaction was carried out with mechanical stirring under vacuum 1187 Pa (8.9 Torr) at about 140° C. (about 3 hours). The reaction mixture was allowed to cool to about 90° C. and sodium hydroxide (50% solution in water) was added to neutralize acid and stirred for at least fifteen minutes. The vacuum was broken and the reaction mixture was then diluted with deionized water and filtered through a 0.2 μm filter to yield a crude isosorbide containing 44.1% isosorbide, 0.115% isomannide, and no isoidide (not detected).

Subsequently, the crude isosorbide was subjected to incomplete purification by applying several purification steps substantially as outlined in copending and commonly-assigned International Patent Application No. WO 2014070371 A1). The crude isosorbide was ultrafiltered with a polyethersulfone membrane (Sepro PES5™, Sepro Membranes, Inc., Oceanside, Calif.) at room temperature to reduce the content of polymeric residue (molecular weight greater than 5000), providing an intermediate process stream. Ion exclusion chromatography on the ultrafiltered isosorbide was carried out by simulated moving bed ion exclusion using a strong acid resin in the sodium form (Dow 99/310Na™, Dow Chemical Co., Midland, Mich.) at room temperature, providing another intermediate process stream. The isosorbide was then subjected to ion exchange polishing using strong acid and strong base resins (Dow 88™ and Dow 22™, respectively, in columns arranged in series) at room temperature, providing a third intermediate process stream. The isosorbide solution was contacted with granular activated carbon (Calgon CPG™, Calgon Carbon, Pittsburgh, Pa.) at room temperature to yield a fourth intermediate process stream, an isosorbide composition containing 36.5 wt % water, isosorbide (44.1 wt %), isomannide (0.112 wt %), and sorbitans (5.0-5.7 wt %). The balance of the material, approximately 14 wt %, comprised unknown high molecular weight compounds observed but not characterized. The weight percent ratio of isosorbide to sorbitans was 7.7/1 to 8.8/1. Isoidide was not detected in the isosorbide composition. Compositional analysis was carried out after derivatization with pyridine and acetic anhydride at 70° C. using a J&W DB-5 MS UI column (30 m×0.25 mm×0.25 um) on an Agilent 7890 gas chromatograph equipped with an FID detector; water was quantified by volumetric Karl Fischer titration. The incompletely purified isosorbide composition contained about 5% sorbitans and was not distilled or subjected to any heat treatment until the composition was epimerized in examples 2-5.

EXAMPLE 2

Sufficient sodium hydroxide co-catalyst was added to the isosorbide composition produced in example 1 to adjust the pH to 10 to produce an isosorbide feedstock containing one or more sorbitans ("epimerization reactor feed") having a water content of about 50%. The isosorbide feedstock containing one or more sorbitans was fed with hydrogen (2000 psi, 17.24 MPa) into a stainless steel reactor (1.58 cm×43 cm; total volume 84.3 mL) containing Raney nickel co-catalyst (30 mL) to carry out epimerization. The reactor comprised a stainless steel tube (1.58 cm diameter, 43 cm length, total volume 84.3 mL). Epimerization was carried out continuously for approximately 3,600 hours while varying the reactor temperature, flow rate (liquid hourly space velocity, LHSV), and reactor pressure. Samples of reactor product (epimerization product comprising isoidide and hydrodeoxygenation products) were analyzed for isohexides and sorbitans and the mass yield of isoidide and isohexide mass loss due to mass loss of isohexides relative to isohexides in the isosorbide feedstock containing one or more sorbitans was calculated for each sample.

EXAMPLE 3

Epimerization experiments were conducted to optimize reactor conditions and determine main effects of the primary reaction variables, temperature, LHSV, and pressure, with respect to isoidide yield and total isohexide mass loss from an isosorbide containing one or more sorbitans. Hydrogen flow rate was kept constant at 1000 mL/minute. The pH of the isosorbide composition was adjusted to 10. Two simple three factorial design of experiments were executed according to the procedures outlined above and the data combined into a single response surface using Design-Expert 9 software (Stat-Ease, Inc., Minneapolis, Minn.). Tables 3.1 show the experimental variables used in this pair of three-factor designed experiments.

TABLE 3.1

Three factor designed experiment variables of first and second three-factor designed experiments in epimerization of an isosorbide containing one or more sorbitans to an epimerization product comprising isoidide and hydrodeoxygenation products. Hydrogen flow rate was 1000 mL/minute and the pH of the reactor feed was 10.

|  | Low | Center | High |
|---|---|---|---|
| First design |  |  |  |
| Reactor Temp. (° C.) | 180 | 200 | 220 |
| LHSV (-hr) | 0.5 | 1.25 | 2.0 |
| Pressure (psi/bar) | 500 psi (34.5 bar) | 1000 psi (68.0 bar) | 1500 psi (103.4 bar) |
| Second design |  |  |  |
| Reactor Temp. (° C.) | 200 | 225 | 250 |
| LHSV (-hr) | 2.0 | 3.0 | 4.0 |
| Pressure | 1500 psi (103.4 bar) | 1750 psi (120.6 bar) | 2000 psi (137.9 bar) |

The two-way interaction of temperature and flow rate (LHSV) appeared to be the most significant factor for both isoidide yield and isohexide mass loss (Table 3.2). The reactor pressure simply amplified the effects of temperature and flow rate.

TABLE 3.2

Regression analysis of data from the pair of three-factor designed experiments of Table 3.1. Negative values for isohexide mass loss are desirable.

| Model equation coefficient | Yield (isoidide from total isohexides) | Isohexide mass loss (from total isohexides) |
|---|---|---|
| Temperature | 3.2 | 14.0 |
| Flow (LHSV) | 3.1 | −8.4 |
| Pressure | 0.6 | −3.2 |
| Temperature × Flow | 25.4 | −12.9 |
| Temperature × Pressure | 15.8 | −5.9 |
| Flow × Pressure | −13.0 | 2.8 |
| Temperature$^2$ | −23.5 | 12.0 |

EXAMPLE 4

Based on the first designs, a series of epimerization experiments was carried out by contacting incompletely purified isosorbide composition containing one or more sorbitans with Raney nickel catalyst at four flow rates (0.5, 1.0, 2.0, 4.0 mL feed/hr/mL cat, LHSV) and three temperatures (210, 230, 250° C.) to epimerize the isosorbide to form an epimerization product comprising isoidide and hydrodeoxygenation products. The pH of the isosorbide composition was adjusted to 10, the hydrogen pressure was 2000 psi (13.79 MPa) and the hydrogen flow was 1000 mL/minute (Table 4.1). The isosorbide composition contained about 5% sorbitans (1,5-sorbitan; 1,4-sorbitan; 2,5-sorbitan; 3,6-sorbitan).

TABLE 4.1

Conversion over Raney nickel of isosorbide containing one or more sorbitans to isoidide composition comprising an epimerization product comprising isoidide and hydrodeoxygenation products. Yield is expressed as weight percent isoidide yield from isohexide. Isohexide mass loss is the same as mass loss in co-pending Patent Cooperation Treaty Publication No. WO2013125950 A1.

| # | Temp ° C. | LHSV (-hr) | Isoidide Yield (wt %) | Isohexide mass loss (wt %) |
|---|---|---|---|---|
| 1468 | 210 | 0.5 | 48.8 | 0 |
| 1492 | 210 | 0.5 | 49.7 | 0 |
| 1612 | 210 | 0.5 | 49.4 | 0 |
| 1540 | 210 | 1.0 | 32.9 | 0 |
| 1618 | 210 | 2.0 | 20.3 | 0 |
| 1546 | 210 | 4.0 | 11.1 | 1.6 |
| 1636 | 230 | 0.5 | 43.2 | 12.3 |
| 1660 | 230 | 1.0 | 49.8 | 4.1 |
| 1665 | 230 | 2.0 | 40.1 | 2.8 |
| 1642 | 230 | 4.0 | 29.9 | 0 |
| 1684 | 250 | 0.5 | 0.2 | 43.9 |
| 1708 | 250 | 1.0 | 26.1 | 24.5 |
| 1712 | 250 | 2.0 | 43.7 | 9.7 |
| 1714 | 250 | 3.0 | 44.2 | 6.8 |
| 1690 | 250 | 4.0 | 41.9 | 4.7 |

Table 4.1 shows, surprisingly, that isoidide could be synthesized by epimerization of the isosorbide containing one or more sorbitans with little or no isohexide mass loss (reactions #1468, 1692, and 1612).

EXAMPLE 5

A series of epimerization experiments was carried out by contacting isosorbide compositions (containing 4.4 to 5.57% sorbitans) with Raney nickel at certain combinations of six flow rates (0.5, 0.75, 1.0, 1.5, 1.75, 2 mL feed/hr/mL cat, LHSV) and five temperatures (200, 210, 217.5, 230, 250° C.) to epimerize the isosorbide to isoidide. The feed pH was adjusted to 10, the hydrogen pressure was 2000 psi (13.79 MPa) and the hydrogen flow was 1000 mL/minute (Tables 5.1 and 5.2). The isosorbide composition used from hour 1868 to 2701 (Table 5.1) contained 44.9% total isohexides and 5.57% total sorbitans (isohexide/sorbitan ratio of 8.06).

TABLE 5.1

Conversion of isosorbide containing one or more sorbitans to an epimerization product comprising isoidide and hydrodeoxygenation products. Yield is expressed as weight percent isoidide yield from isohexides, isohexide mass loss indicates the mass loss of isohexides relative to starting isohexides, sorbitan loss indicates the decomposition of sorbitans.

| # | Temp (° C.) | LHSV (-hr) | Yield (wt %) | Isohexide loss (wt %) | Sorbitan loss (wt %) | Isoidide/ isosorbide/ isomannide |
|---|---|---|---|---|---|---|
| 1868 | 210 | 0.5 | 43.0 | 0.66 | 81.1 | 44/50/7 |
| 1964 | 230 | 1 | 46.5 | 3.79 | 87.8 | 51/43/6 |
| 1988 | 230 | 1 | 46.2 | 3.46 | 87.8 | 50/43/7 |
| 2012 | 230 | 1 | 44.7 | 4.22 | 87.0 | 49/44/7 |
| 2036 | 230 | 1 | 44.3 | 3.80 | 85.7 | 48/45/7 |
| 2060 | 230 | 1 | 45.5 | 2.80 | 85.4 | 49/45/7 |
| 2132 | 230 | 1 | 43.4 | 2.91 | 82.1 | 46/47/7 |
| 2156 | 230 | 1 | 44.1 | 1.96 | 81.4 | 46/47/7 |
| 2197 | 230 | 1 | 40.0 | 5.22 | 84.2 | 45/47/8 |
| 2269 | 230 | 1 | 41.8 | 3.75 | 82.0 | 46/46/8 |
| 2293 | 230 | 1 | 41.4 | 3.85 | 81.8 | 45/47/8 |
| 2317 | 230 | 1 | 40.4 | 4.35 | 80.9 | 45/47/8 |
| 2341 | 230 | 1 | 39.9 | 4.69 | 80.7 | 45/47/8 |
| 2365 | 230 | 1 | 39.0 | 4.90 | 79.6 | 44/48/8 |
| 2437 | 230 | 1 | 40.0 | 4.29 | 79.2 | 44/48/8 |
| 2461 | 230 | 1 | 39.5 | 4.34 | 78.6 | 44/48/8 |
| 2485 | 230 | 1 | 34.0 | 9.61 | 80.8 | 43/49/8 |
| 2509 | 230 | 1 | 38.3 | 4.15 | 76.9 | 42/50/8 |
| 2533 | 230 | 1 | 33.8 | 8.53 | 78.7 | 42/50/8 |
| 2605 | 230 | 1 | 36.4 | 4.63 | 75.7 | 41/51/8 |
| 2629 | 230 | 1 | 36.2 | 4.38 | 74.8 | 40/52/8 |
| 2677 | 250 | 1 | 39.5 | 13.23 | 97.1 | 56/36/8 |
| 2687 | 250 | 1 | 39.7 | 13.13 | 97.1 | 56/36/8 |
| 2701 | 250 | 1 | 40.3 | 12.56 | 96.8 | 56/36/8 |

The isosorbide composition used from hour 2741 to 3641 (Table 5.2) contained 41.3% total isohexides and 4.40% total sorbitans (isohexide/sorbitan ratio of 9.39).

TABLE 5.2

Conversion of isosorbide containing one or more sorbitans to isoidide. "Yield" is expressed as weight percent isoidide yield from isohexides, "Isohexide mass" loss indicates the mass loss of isohexides relative to starting isohexides, "Sorbitan loss" indicates the decomposition of sorbitans.

| # | Temp (° C.) | LHSV (-hr) | Yield (wt %) | Isohexide mass loss (wt %) | Sorbitan loss (wt %) | Isoidide/ isosorbide/ isomannide |
|---|---|---|---|---|---|---|
| 2741 | 230 | 1 | 30.3 | 3.51 | 72.7 | 33/60/7 |
| 2765 | 230 | 1 | 30.8 | 2.77 | 70.9 | 33/60/7 |
| 2831 | 230 | 1 | 26.7 | 22.22 | 95.8 | 58/37/6 |
| 2855 | 230 | 1 | 27.6 | 21.56 | 95.4 | 58/37/6 |
| 2879 | 230 | 1 | 28.3 | 21.11 | 95.3 | 58/37/6 |
| 2897 | 230 | 1 | 28.7 | 20.54 | 95.1 | 57/37/6 |
| 2969 | 230 | 1 | 30.5 | 19.20 | 98.0 | 57/37/6 |
| 2993 | 210 | 1 | 43.0 | 3.89 | 66.2 | 47/47/6 |
| 3017 | 200 | 1 | 36.3 | 2.20 | 46.9 | 38/56/6 |
| 3041 | 200 | 1 | 36.1 | 2.32 | 45.8 | 38/56/6 |
| 3065 | 200 | 0.5 | 31.6 | 14.29 | 82.2 | 48/45/6 |
| 3137 | 200 | 0.5 | 45.2 | 3.62 | 76.4 | 49/45/6 |
| 3161 | 200 | 0.5 | 40.6 | 2.40 | 58.3 | 43/51/6 |
| 3185 | 200 | 0.75 | 36.4 | 7.05 | 61.1 | 44/50/6 |
| 3209 | 200 | 0.75 | 36.2 | 7.22 | 46.5 | 44/50/6 |
| 3233 | 210 | 1 | 38.4 | 8.68 | 74.6 | 49/45/6 |
| 3305 | 210 | 1 | 38.7 | 8.67 | 75.4 | 49/45/6 |
| 3401 | 210 | 1.5 | 39.4 | 3.74 | 61.9 | 43/51/6 |
| 3475 | 210 | 1.5 | 38.8 | 3.71 | 60.4 | 43/51/6 |
| 3521 | 210 | 1.75 | 37.2 | 3.00 | 54.0 | 40/54/6 |
| 3545 | 210 | 1.75 | 37.1 | 3.22 | 54.8 | 40/54/6 |
| 3569 | 210 | 1.75 | 37.2 | 3.13 | 54.7 | 40/54/6 |
| 3641 | 217.5 | 2 | 39.2 | 5.40 | 69.0 | 45/49/6 |

Under these conditions, we were able to reach equilibrium production of isoidide and effect substantial reduction in sorbitans in the isosorbide feed.

Although the present invention has been described generally and by way of examples, it is understood by those persons skilled in the art that the invention is not necessarily limited to the embodiments specifically disclosed, and that modifications and variations can be made without departing from the spirit and scope of the invention. Thus, unless changes otherwise depart from the scope of the invention as defined by the following claims, they should be construed as included herein.

The invention claimed is:

1. A method for synthesizing isoidide, comprising,
   providing an isosorbide containing one or more sorbitans; and,
   epimerizing the isosorbide to form an epimerization product comprising isoidide and hydrodeoxygenation products.

2. The method of claim 1, wherein the isosorbide containing one or more sorbitans is obtained from one or more intermediate process streams in a process for producing at least a technical grade isosorbide product through the dehydration of sorbitol, or from adding sorbitans to a technical grade or better isosorbide.

3. The method of claim 2, wherein the isosorbide containing one or more sorbitans is obtained by adding one or more sorbitans to one or more intermediate process streams containing isosorbide, or by adding additional of the one or more sorbitans to one or more intermediate process streams containing both isosorbide and one or more sorbitans.

4. The method of claim 2, wherein the isosorbide containing one or more sorbitans is obtained from one or more of incompletely purified isosorbide, partially purified isosorbide, intermediately purified isosorbide streams, recycled distillation bottoms from isosorbide manufacturing, isosorbide crude reaction mixture, extracts from a series of simulated moving bed ion exclusion isosorbide purification steps, combined ion-excluded, ion-exchanged isosorbide mixtures, degassed isosorbide residue, commercially available isosorbide and combinations of any thereof.

5. The method of claim 1, wherein epimerization is carried out in the presence of hydrogen and an epimerization catalyst selected from the group consisting of nickel supported on diatomaceous earth, a supported nickel hydrogenation catalyst, Raney nickel, ruthenium on carbon, ruthenium on a support, ruthenium on aluminum oxide, palladium on carbon, platinum on carbon, rhodium on carbon, gold on carbon, nickel on silica dioxide, palladium hydroxide on carbon, Pearlman's catalyst, and combinations of any thereof to form the epimerization product comprising isoidide and hydrodeoxygenation products.

6. The method of claim 5, further comprising selecting an intermediate process stream or streams, selecting an intermediate process stream or streams and adding one or more sorbitans thereto, or adding sufficient sorbitans to a technical grade or better isosorbide, such that the amount of sorbitans in the resultant isosorbide is greater than 0.1%, greater than 0.2%, greater than 0.5%, greater than 1%, greater than 2%, greater than 3%, greater than 4%, greater than 5%, greater than 6%, greater than 7%, greater than 8%, greater than 9%, greater than 10% and up to 20% sorbitans.

7. The method of claim 1, wherein the ratio of isohexide content to sorbitan content (in weight percent) in the isosorbide ranges from one to two hundred.

8. The method of claim 1, wherein the yield of isoidide produced in epimerization of isosorbide ranges from 27-58 wt %; wherein the yield is defined as the amount of isoidide relative to the sum of the amounts isoidide, isosorbide, and isomannide; and wherein the amounts are determined using a DB-5 MS UI column (30 m×0.25 mm×0.25 um) on a gas chromatograph equipped with an FID detector.

9. The method of claim 1, wherein the yield of isoidide, is at least 27 wt. %, is at least 28 wt. %, is at least 29 wt. %, is at least 30 wt. %, is at least 31 wt. %, is at least 32 wt. %, is at least 33 wt. %, is at least 34 wt. %, is at least 35 wt. %, is at least 36 wt. %, is at least 37 wt. %, is at least 38 wt. %, is at least 39 wt. %, is at least 40 wt. %, is at least 41 wt. %, is at least 42 wt. %, is at least 43 wt. %, is at least 44 wt. %, is at least 45 wt. %, is at least 46 wt. %, is at least 47 wt. %, is at least 48 wt. %, is at least 49 wt. %, is at least 50 wt. %, is at least 51 wt. %, is at least 52 wt. %, is at least 53 wt. %, is at least 54 wt. %, is at least 55 wt. %, is at least 56 wt. %, is at least 57 wt. %, is at least 58 wt. %.

10. The method of claim 1, wherein the content of sorbitans in the isosorbide feedstock containing one or more sorbitans is greater than the content of sorbitans in the epimerization reactor product comprising isoidide.

11. The method of claim 1, wherein the epimerization of an isosorbide containing one or more sorbitans is carried out over nickel at a pressure of about 2000 psi (13.79 MPa), a hydrogen flow of about 1000 mL/minute, reaction temperature of 225-235° C., and at a liquid hourly space velocity of about 1/hr.

* * * * *